US012161837B2

(12) United States Patent
Prudden et al.

(10) Patent No.: US 12,161,837 B2
(45) Date of Patent: *Dec. 10, 2024

(54) DELIVERY DEVICE WITH NOISE REDUCING COMPONENT

(71) Applicant: Becton, Dickinson and Company, Franklin Lakes, NJ (US)

(72) Inventors: John Prudden, Manchester, MA (US); Andrew Allegretti, New York, NY (US); Jean-Pierre Raphael Karam, Wyckoff, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 974 days.

This patent is subject to a terminal disclaimer.

(21) Appl. No.: 17/174,367

(22) Filed: Feb. 12, 2021

(65) Prior Publication Data
US 2021/0162120 A1    Jun. 3, 2021

Related U.S. Application Data

(63) Continuation of application No. 16/035,215, filed on Jul. 13, 2018, now Pat. No. 10,946,136.
(Continued)

(51) Int. Cl.
*A61M 5/14* (2006.01)
*A61M 5/142* (2006.01)
(Continued)

(52) U.S. Cl.
CPC .... *A61M 5/14248* (2013.01); *A61M 5/14566* (2013.01); *F04B 53/003* (2013.01);
(Continued)

(58) Field of Classification Search
CPC .......... A61M 5/14248; A61M 5/14566; A61M 2005/14252; A61M 2005/14268;
(Continued)

(56) References Cited

U.S. PATENT DOCUMENTS 5,407,034 A    4/1995 Vydra
8,911,404 B2    12/2014 Kim
(Continued)

FOREIGN PATENT DOCUMENTS

KR    20140125196 A    10/2014
WO    2010041261 A1    4/2010
WO    2011159930 A2    12/2011

OTHER PUBLICATIONS

Extended European Search Report dated Nov. 9, 2018, which issued in the counterpart European Patent Application No. 18182736.1.

*Primary Examiner* — Amber R Stiles
(74) *Attorney, Agent, or Firm* — Dickinson Wright PLLC

(57) ABSTRACT

A delivery device for delivering a medication to a patient includes a catheter with a catheter insertion mechanism, a housing, and a base with a surface for supporting a pump mechanism. A noise dampening member in or on the device inhibits noise and vibrations from the pump mechanism from transferring through the base and housing. The noise dampening member can be an elastomer that is coated on or adhered to the base. The noise dampening member can be molded in or on the base in a suitable location to dampen noise produced by the mechanical component. The noise dampening member can be between the base and the mechanical component or spaced from the mechanical component. The noise dampening member can be molded in a recessed area formed in the base and can have a top face that is recessed, aligned with or project from the top face of the base.

19 Claims, 12 Drawing Sheets

Related U.S. Application Data

(60) Provisional application No. 62/533,276, filed on Jul. 17, 2017.

(51) Int. Cl.
    *A61M 5/145*     (2006.01)
    *F04B 53/00*     (2006.01)
    *F04B 53/16*     (2006.01)

(52) U.S. Cl.
    CPC ... *F04B 53/16* (2013.01); *A61M 2005/14252* (2013.01); *A61M 2005/14268* (2013.01); *A61M 2205/0216* (2013.01); *A61M 2205/42* (2013.01)

(58) Field of Classification Search
    CPC ...... A61M 2205/0216; A61M 2205/42; A61M 5/142; F04B 53/003; F04B 53/16
    See application file for complete search history.

(56) References Cited

U.S. PATENT DOCUMENTS

| | | | |
|---|---|---|---|
| 10,946,136 B2 * | 3/2021 | Prudden | A61M 5/14566 |
| 2008/0091139 A1 * | 4/2008 | Srinivasan | A61M 5/30 604/68 |
| 2011/0202005 A1 * | 8/2011 | Yodfat | A61M 5/14248 604/151 |
| 2015/0003966 A1 | 1/2015 | Duquette | |

* cited by examiner

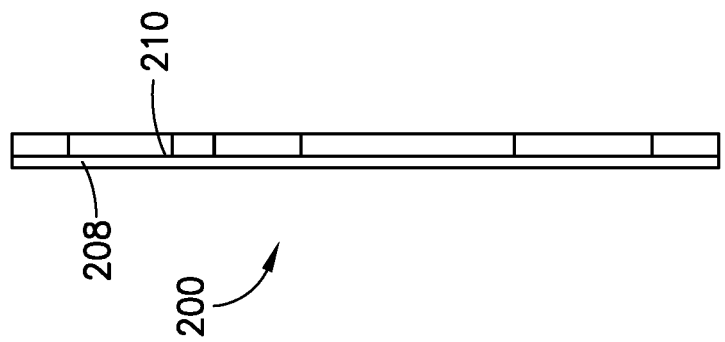
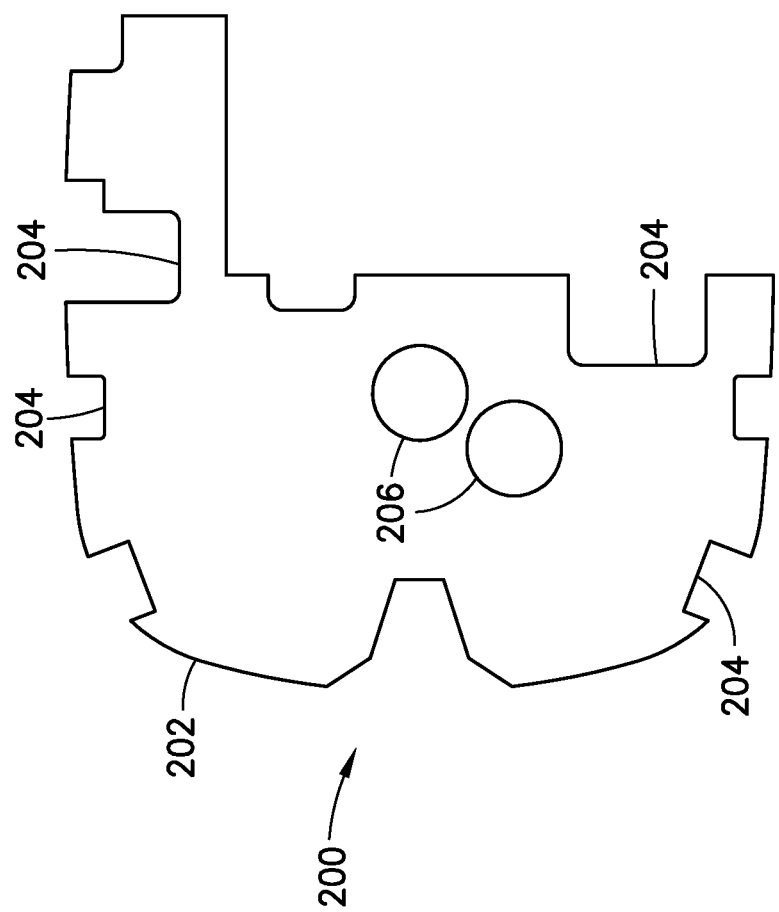

DELIVERY DEVICE WITH NOISE REDUCING COMPONENT

This application is a continuation application of U.S. Ser. No. 16/035,215, filed on Jul. 13, 2018, which claims priority to U.S. Provisional Patent Application No. 62/533,276 filed on Jul. 17, 2017, which are hereby incorporated by reference in their entireties.

FIELD OF THE INVENTION

The present invention relates to a delivery device for a medication, and more particularly, to medical delivery devices and apparatus with a dispensing mechanism having a vibration and/or noise reducing component.

BACKGROUND

Diabetes is a group of diseases characterized by high levels of blood glucose resulting from the inability of diabetic patients to maintain proper levels of insulin production when required. Persons with diabetes will require some form of daily insulin therapy to maintain control of their glucose levels. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. The main goal of diabetes treatment is to control the diabetic patient's blood glucose or sugar level. However, maintaining proper diabetes management may be complicated because it has to be balanced with the activities of the diabetic patient.

For the treatment of type 1 diabetes, there are two principal methods of daily insulin therapy. In the first method, diabetic patients use syringes or insulin pens to self-inject insulin when needed. This method requires a needle stick for each injection, and the diabetic patient may require three to four injections daily. The syringes and insulin pens that are used to inject insulin are relatively simple to use and cost effective.

Another effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs.

Infusion pump therapy requires an infusion cannula, typically in the form of an infusion needle or a flexible catheter, that pierces the diabetic patient's skin and through which, infusion of insulin takes place. Infusion pump therapy offers the advantages of continuous infusion of insulin, precision dosing, and programmable delivery schedules.

In infusion therapy, insulin doses are typically administered at a basal rate and in a bolus dose. When insulin is administered at a basal rate, insulin is delivered continuously over 24 hours in order to maintain the diabetic patient's blood glucose levels in a consistent range between meals and rest, typically at nighttime. Insulin pumps may also be capable of programming the basal rate of insulin to vary according to the different times of the day and night. In contrast, a bolus dose is typically administered when a diabetic patient consumes a meal, and generally provides a single additional insulin injection to balance the consumed carbohydrates. Insulin pumps may be configured to enable the diabetic patient to program the volume of the bolus dose in accordance with the size or type of the meal that is consumed by the diabetic patient. In addition, insulin pumps may also be configured to enable the diabetic patient to infuse a correctional or supplemental bolus dose of insulin to compensate for a low blood glucose level at the time when the diabetic patient is calculating the bolus dose for a particular meal that is to be consumed.

Insulin pumps advantageously deliver insulin over time rather than in single injections, typically resulting in less variation within the blood glucose range that is recommended. In addition, insulin pumps may reduce the number of needle sticks which the diabetic patient must endure, and improve diabetes management to enhance the diabetic patient's quality of life.

Typically, regardless of whether a diabetic patient uses multiple direct injections (MDIs) or a pump, the diabetic patient takes fasting blood glucose medication (FBGM) upon awakening from sleep, and also tests for glucose in the blood during or after each meal to determine whether a correction dose is required. In addition, the diabetic patient may test for glucose in the blood prior to sleeping to determine whether a correction dose is required, for instance, after eating a snack before sleeping.

To facilitate infusion therapy, there are generally two types of insulin pumps, namely, conventional pumps and patch pumps. Conventional pumps require the use of a disposable component, typically referred to as an infusion set, tubing set or pump set, which conveys the insulin from a reservoir within the pump into the skin of the user. The infusion set consists of a pump connector, a length of tubing, and a hub or base from which a cannula, in the form of a hollow metal infusion needle or flexible plastic catheter extends. The base typically has an adhesive that retains the base on the skin surface during use. The cannula can be inserted into the skin manually or with the aid of a manual or automatic insertion device. The insertion device may be a separate unit required by the user.

Another type of insulin pump is a patch pump. Unlike a conventional infusion pump and infusion set combination, a patch pump is an integrated device that combines most or all of the fluidic components, including the fluid reservoir, pumping mechanism and mechanism for automatically inserting the cannula, in a single housing which is adhesively attached to an infusion site on the patient's skin, and does not require the use of a separate infusion or tubing set. A patch pump containing insulin adheres to the skin and delivers the insulin over a period of time via an integrated subcutaneous cannula. Some patch pumps may wirelessly communicate with a separate controller device (as in one device sold by Insulet Corporation under the brand name OmniPod®), while others are completely self-contained. Such devices are replaced on a frequent basis, such as every three days, when the insulin reservoir is exhausted or complications may otherwise occur, such as restriction in the cannula or the infusion site.

As patch pumps are designed to be a self-contained unit that is worn by the diabetic patient, it is preferable to be as small as possible so that it does not interfere with the activities of the user. Thus, in order to minimize discomfort to the user, it would be preferable to minimize the overall thickness of the patch pump. However, in order to minimize the thickness of the patch pump, its constituent parts should be reduced as much as possible. One such part is the insertion mechanism for automatically inserting the cannula into the user's skin.

To minimize the height of the insertion mechanism, conventional insertion mechanisms are generally configured to insert the cannula at an acute angle from the surface of the skin, e.g. 30-45 degrees. However, it is generally preferable to insert the cannula perpendicular or close to the perpendicular from the surface of the skin since this would require the minimum length of cannula insertion. In other words, with the minimum length of cannula being inserted into the user's skin, the user can experience greater comfort and fewer complications, such as premature kinking of the cannula.

A common problem or concern with patch pumps and other electrically operated drug delivery devices is the vibration and noise produced during operation of the pump mechanism. The movement of the motor and pump mechanism can result in vibrations that can be perceived by the user when attached to the skin and can produce audible sounds that can be heard by others.

Accordingly, a need exists for an improved delivery device for use in a limited space environment, such as in the patch pump, that can reduce the vibration and sounds emitted by the device during use without interfering with the normal operation of the device.

SUMMARY

One aspect of the present invention is a delivery device, such as a patch pump, catheter device, infusion pump, or other delivery device for delivering a substance to a patient. The substance can be insulin, drugs, or pharmaceutical. The delivery device has movable components and is constructed to reduce or dampen the vibration and/or noise produced by mechanical components of the device during use. The device in one embodiment is a patch pump or other delivery device where the mechanical components of the delivery device that are responsible for producing vibrations and/or noise are isolated or shielded by a noise reducing component. The noise reducing component is a vibration and/or noise dampening member to inhibit vibrations and noise from transferring to the base or housing of the device. In one embodiment the noise dampening member is formed from a noise dampening material positioned between the base and/or housing and the mechanical component of the delivery mechanism. In other embodiments, the noise dampening member can be provided on other locations in or on the base or at selected locations on the inner surface of the housing. The noise dampening member can be oriented on a surface within the cavity formed by the base and cover or on an outer surface of the device in an area to dampen noise from components of the device.

The aspects of the present invention are achieved by providing delivery device, such as a catheter delivery device, having a housing, base with a noise reducing component, and mechanical components for delivering the pharmaceutical or drug to a patient through a cannula, where the cannula can be steel cannula or flexible catheter. In one embodiment, the base includes at least one selected area on the top face of the base with a vibration and/or noise dampening material between the base and the mechanical component. The mechanical components of the delivery device are isolated or shielded from the base and housing by the vibration and/or noise dampening material to inhibit vibrations and noise from transferring from the mechanical components to the base or housing. The vibration and/or noise dampening material is oriented and configured to reduce and minimize the perceived noise level and vibration produced by the mechanical components during use.

The various aspects of the present invention are also achieved by providing a method of constructing a delivery device by providing a noise reducing component from a vibration and/or noise dampening material between the mechanical components and the base and/or housing of the delivery device.

The various aspects of the present invention are also achieved by providing a delivery device such as a catheter delivery device, including a housing and a base coupled to the housing and enclosing mechanical components of the delivery device. The mechanical components can include a pump mechanism and gearbox for operating the pump, and a motor for driving the gear box and pump mechanism. The base is configured for supporting the pump mechanism, a catheter and catheter insertion mechanism, and a drive motor connected to a suitable power source such as a battery for driving the pump mechanism. The base has at least one and typically more than one supporting area for the pump, motor and other moving components of the pump mechanism. A vibration and/or noise dampening material is provided in the supporting area between the base and the mechanical component to dampen vibration and noise through the base and housing. In one embodiment, the vibration and/or noise dampening material can be an elastomeric polymer applied to the supporting area of the base.

In one embodiment, the delivery device is a catheter infusion pump assembly having a housing and a base coupled to the housing and defining a cavity. The base has a top face in the cavity and a bottom face. The bottom face is configured for contacting the skin of the patient during use with the catheter inserted into the patient at the infusion site. At least one vibration and noise dampening material is provided in or on the top face of the base. At least one mechanical component of the pump mechanism of the pump assembly is coupled to the top face of the base and can be positioned over or proximate the noise dampening member or spaced from the noise dampening member. The vibration and noise dampening material in one embodiment can be provided in one or more selected locations where the mechanical components of the pump assembly are mounted to absorb vibrations and inhibit vibrations and noise in the base and housing. The vibration and noise dampening member is oriented between the mechanical component and the base. In other embodiments, the noise dampening member can be positioned between the mechanical components and the housing to absorb noise and vibration from the mechanical components.

In one embodiment of the invention, the noise dampening member can be a sheet material or a separately formed member that is applied to a surface of the device and attached to the device in a fixed position. The noise dampening member can have a suitable shape and dimension to cover a selected area of the device and can have an adhesive or mastic layer applied to one side for attaching the noise dampening member to the device. The noise dampening member can have a shape and dimension to cover all or a selected portion of the top face of the base or to the cover. The noise dampening member can be attached a suitable surface within the device or on an outer surface of the device.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 14 is a top view of a noise dampening member in a further embodiment formed as a separate member that can be attached to the device; and FIG. 15 is an end view of the noise dampening member of FIG. 14.

DETAILED DESCRIPTION OF EMBODIMENTS OF THE PRESENT INVENTION

Figure 1:
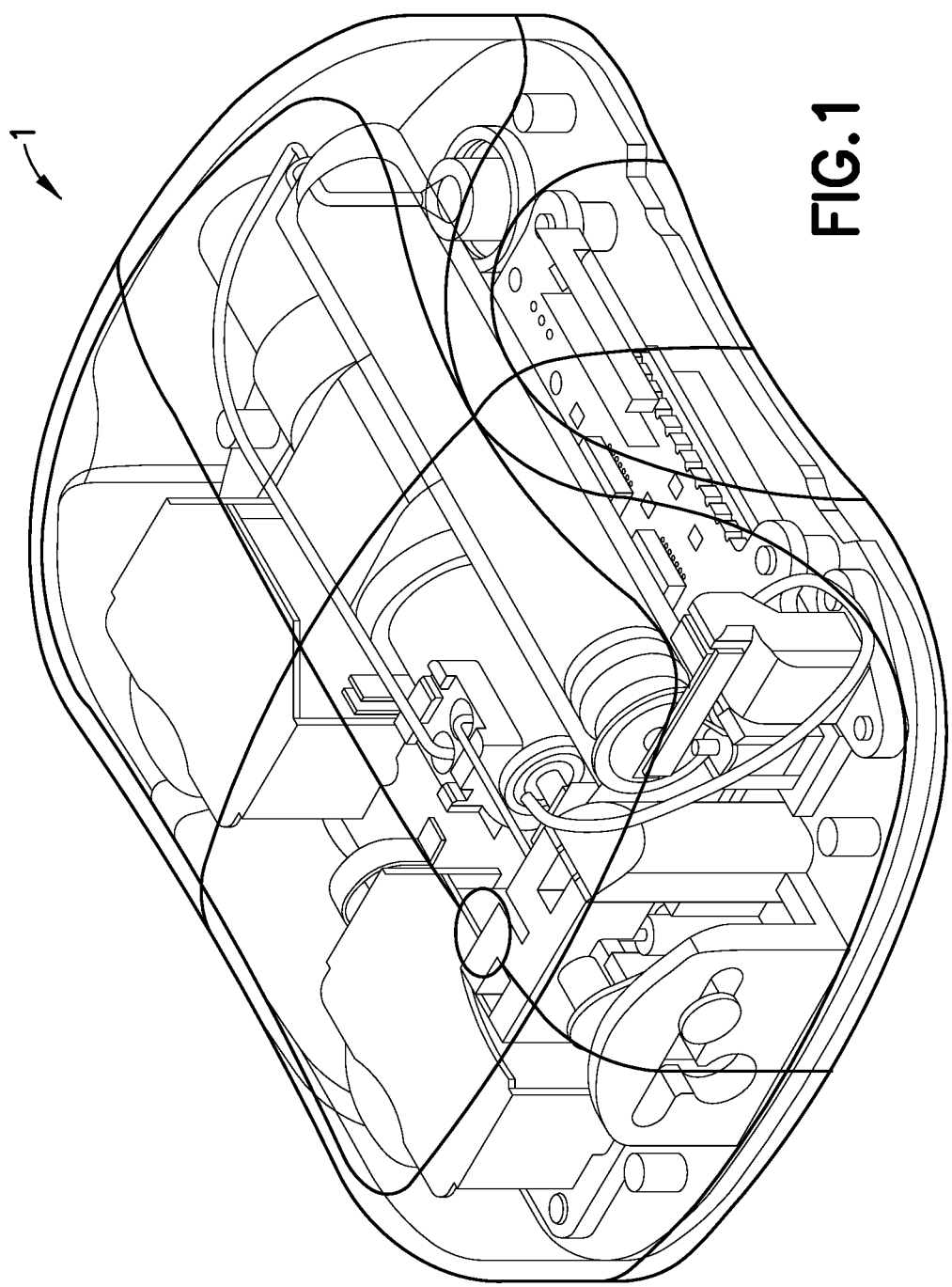
FIG. 1 is a perspective view of a delivery device shown as a patch pump incorporating a low-profile cannula insertion device, illustrated with a transparent cover for clarity.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting. The features discloses in connection with one embodiment can be combined with another embodiment without departing from the scope of the disclosure or the invention.

Figure 2:
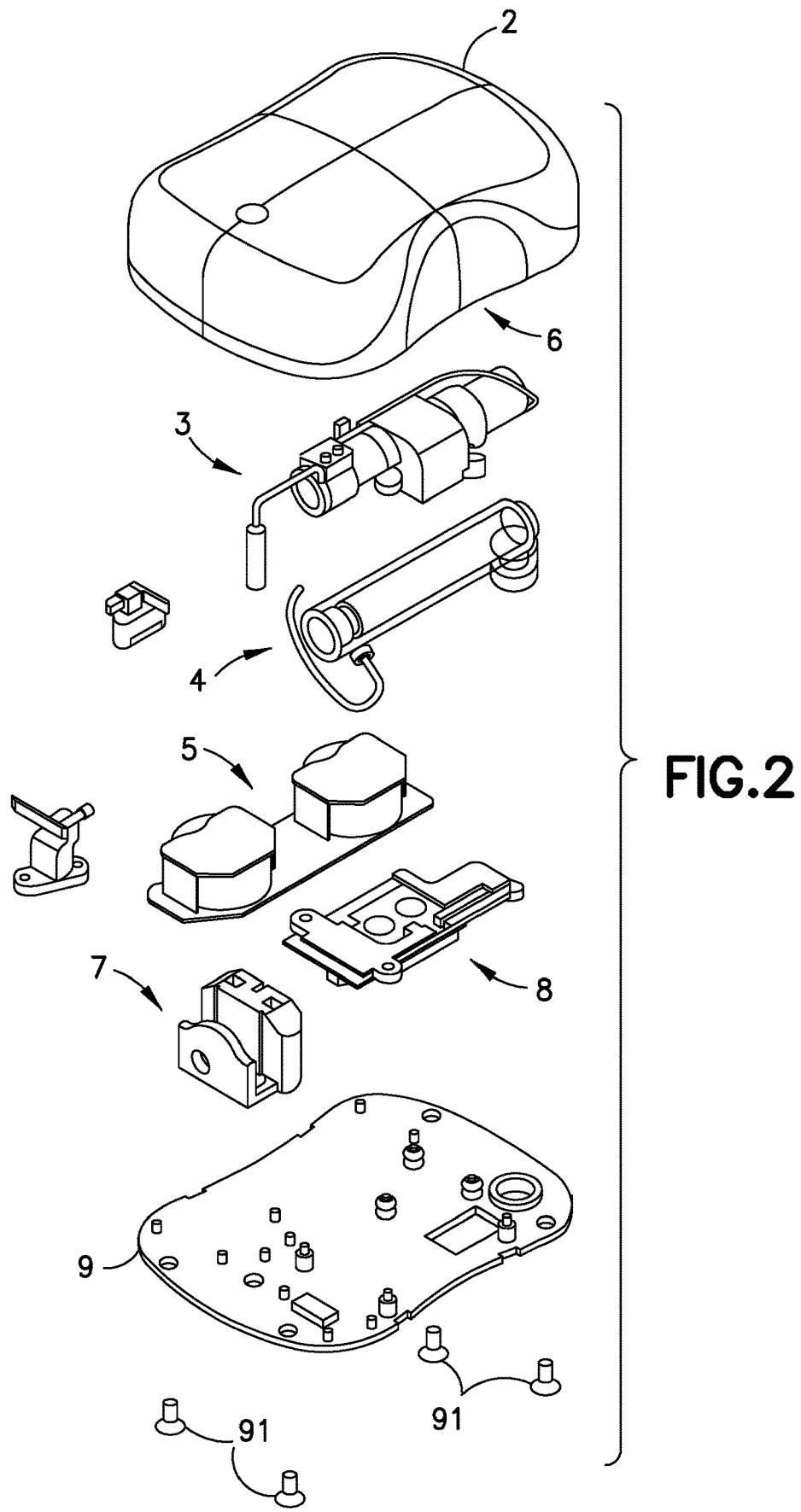
FIG. 2 is an exploded view of the various components of the delivery device of FIG. 1, illustrated with a cover.

FIG. 1 is a perspective view of an exemplary embodiment of the delivery device shown as an infusion pump or a patch pump 1. The patch pump 1 is illustrated with a see-through cover for clarity and illustrates various components that are assembled to form the patch pump 1. FIG. 2 is an exploded view of the various components of the patch pump of FIG. 1, illustrated with a solid cover 2. The various components of the patch pump 1 may include a reservoir 4 for storing insulin, a pump mechanism 3 having a gearbox for pumping a substance such as insulin from the reservoir 4, a power source 5 in the form of one or more batteries, an insertion mechanism 7 for inserting an inserter needle with a catheter into a user's skin, control electronics 8 in the form of a circuit board with optional communications capabilities to outside devices such as a remote controller and computer, including a smart phone, a dose button 6 on the cover 2 for actuating an insulin dose, including a bolus dose, and a base 9 to which various components above may be attached via fasteners 91. The patch pump 1 also includes various fluid connector lines that transfer insulin pumped out of the reservoir 4 to the infusion site.

It should be understood that inserter mechanisms come in various configurations. In some embodiments, the inserter mechanism inserts a soft catheter into the skin. In these embodiments, typically the soft catheter is supported on a rigid insertion needle. The insertion needle is inserted into the skin along with the soft catheter, and then retracted from the skin, leaving the soft catheter in the skin. In other embodiments, a soft catheter is not provided, and the insertion needle remains in the skin and forms a portion of the insulin flow path to deliver insulin until the infusion is finished. Insertion needles are typically hollow, and need to be hollow if they form part of the insulin flow path. However, insertion needles that support a soft catheter and then retract may be solid or hollow. If the insertion needle deploys a soft catheter, and retracts but remains part of the insulin flow path, then the insertion needle should be hollow. However, if the insertion needle deploys a soft catheter and then retracts but does not form part of the insulin flow path, then the insertion needle may be solid or hollow. In either case, the insertion needle is preferably rigid enough to penetrate the skin reliably, but otherwise may be made flexible enough to provide comfort to the user.

Figure 3:
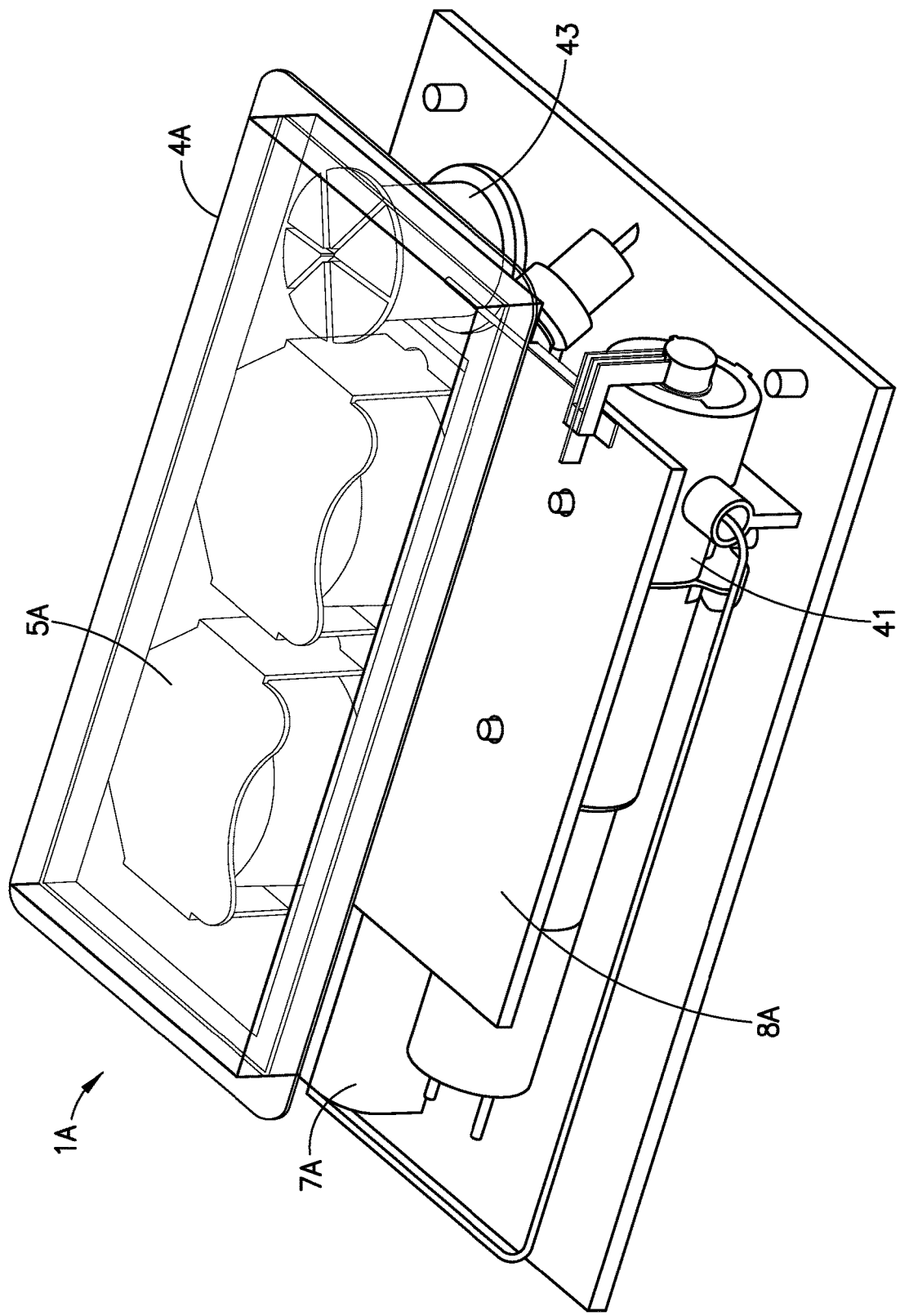
FIG. 3 is a perspective view of an alternative design for a patch pump having a flexible reservoir, illustrated without a cover.

FIG. 3 is a perspective view of an alternative design for a patch pump 1A having a flexible reservoir 4A, and illustrated without a cover. Such arrangement may further reduce the external dimensions of the patch pump 1A, with the flexible reservoir 4A filling voids within the patch pump 1A. The patch pump 1A is illustrated with a conventional cannula insertion device 7A that inserts the cannula, typically at an acute angle, less than 90 degrees, at the surface of a user's skin. The patch pump 1A further comprises: a power source 5A in the form of batteries; a metering sub-system 41 that monitors the volume of insulin and includes a low volume detecting ability; control electronics 8A for controlling the components of the device; and a reservoir fill port 43 for receiving a refill syringe 45 to fill the reservoir 4A.

Figure 4:
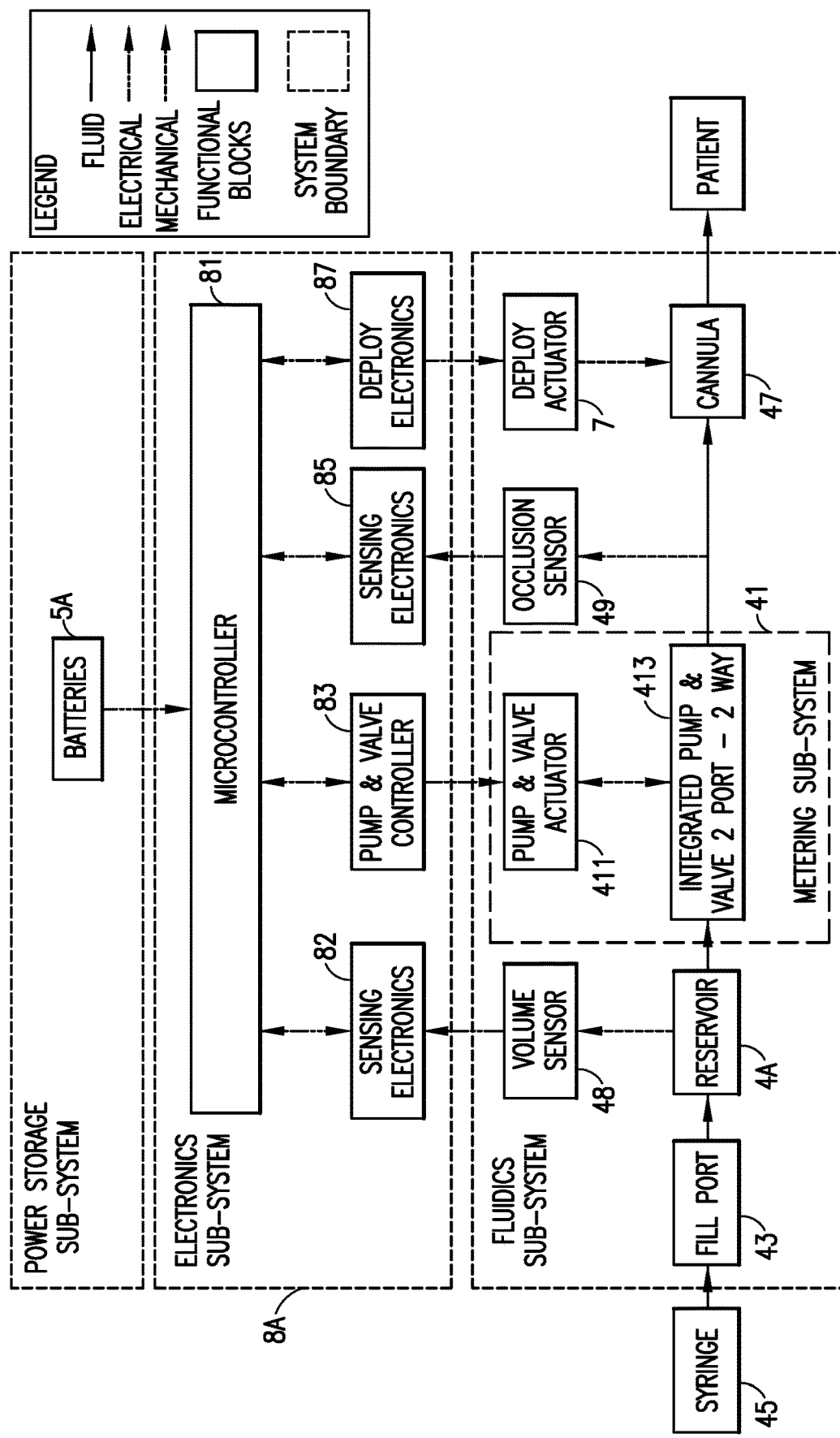
FIG. 4 is a patch-pump fluidic architecture and metering sub-system diagram of the patch pump of FIG. 3.

FIG. 4 is a patch-pump fluidic architecture and metering sub-system diagram of the patch pump 1A of FIG. 3. The power storage sub-system for the patch pump 1A includes batteries 5A. The control electronics 8A of the patch pump 1A may include a microcontroller 81, sensing electronics 82, pump and valve controller 83, sensing electronics 85, and deployment electronics 87 that control the actuation of the patch pump 1A. The patch pump 1A includes a fluidics sub-system that may include a reservoir 4A, volume sensor 48 for the reservoir 4A, a reservoir fill port 43 for receiving a refill syringe 45 to refill the reservoir 4A. The fluidics sub-system may include a metering system comprising a pump and valve actuator 411 and an integrated pump and valve mechanism 413. The fluidics sub-system may further include an occlusion sensor, a deploy actuator, as well as the cannula 47 for insertion into an infusion site on the user's skin. The architecture for the patch pumps of FIGS. 1 and 2 is the same or similar to that which is illustrated in FIG. 4.

Figure 5:
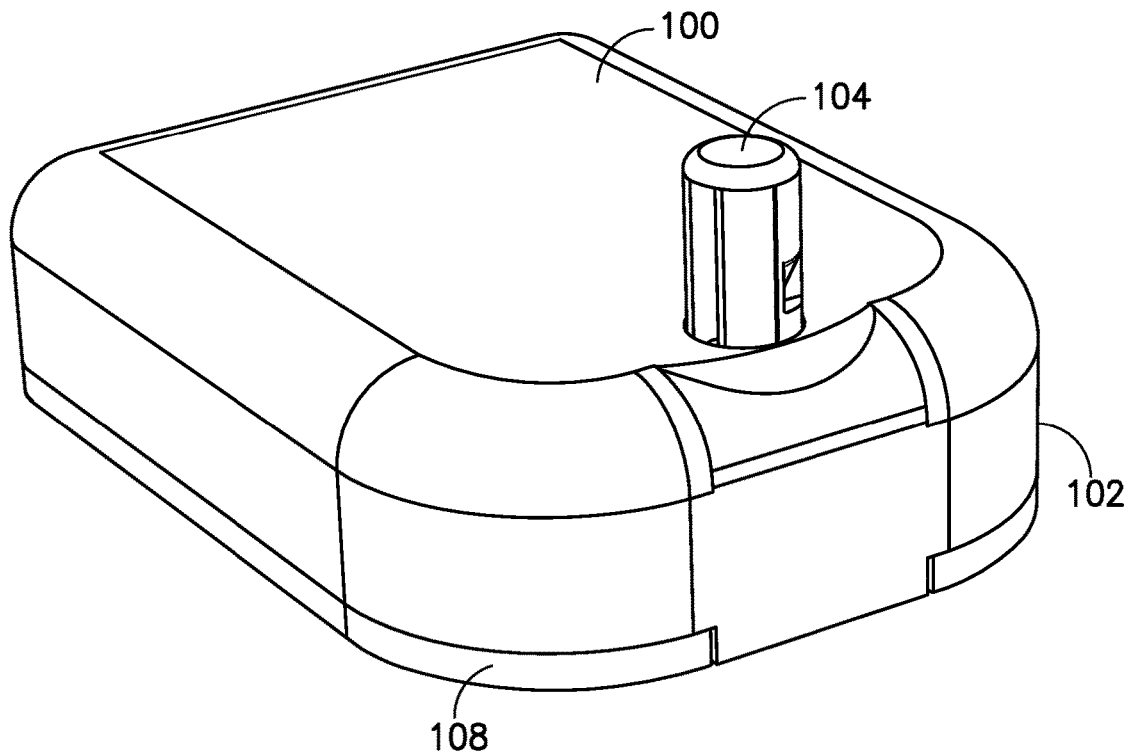
FIG. 5 is perspective view of a delivery device in another embodiment of the invention showing the delivery device including a catheter and insertion needle before being deployed.
Figure 6:
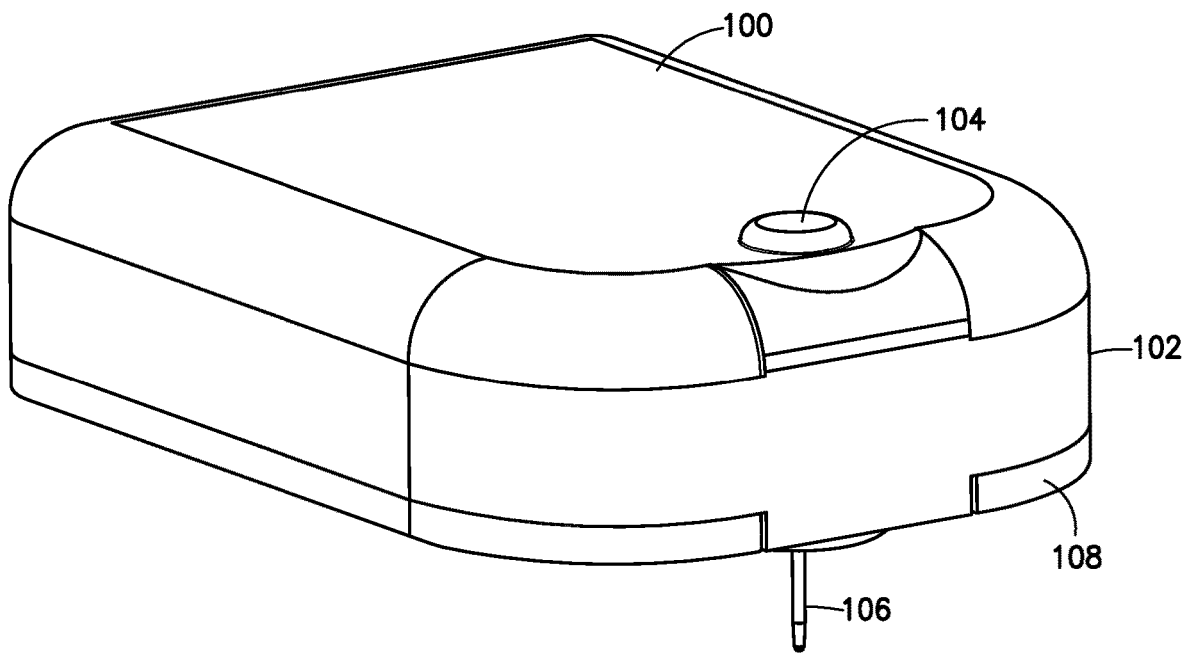
FIG. 6 is a perspective view of the delivery device of FIG. 5 showing the catheter deployed for delivering a substance to a patient.

Referring to FIG. 5 an embodiment of a delivery device 100 is shown having a housing 102 and an actuator button 104 for deploying the delivery cannula shown as a catheter and insertion needle into the patient. The delivery device 100 is typically a patch pump as in FIGS. 1-4. The delivery cannula shown with a catheter insertion mechanism, pump mechanism, and gearbox, operating system such as one or more circuit boards and other components needed to deliver the insulin or other substance to the patient. FIG. 6 is a perspective view of the delivery device 100 after the actuator button 104 is pressed to insert the catheter 106 into the patient for delivering the substance to the patient. The delivery device has bottom wall defined by a base 108 that is coupled to the housing 102 and encloses the mechanical components for the delivery device including the pump and gearbox mechanism, pump motor, insertion needle, and catheter 106. For clarity, the components of the pump and delivery mechanism are not shown in FIGS. 5 and 6. It is to be understood that the pump, pump motor and other components of the delivery device are similar to the embodiment shown in FIGS. 1-4 and are mounted on or attached to the base 108.

In an embodiment the user is able to insert the soft catheter and retract the introducer needle by depressing the actuator button of the device. Generally, no other interaction with the device is needed for catheter deployment and the initiation of medicament delivery. In other embodiments, subsequent to placement of the patch pump on the patient's skin and dosage setting, for example, by a remote device, the only required user interaction with the patch pump to insert the soft catheter, retract the introducer needle, and begin medicament delivery is to depress the button.

Figure 7:
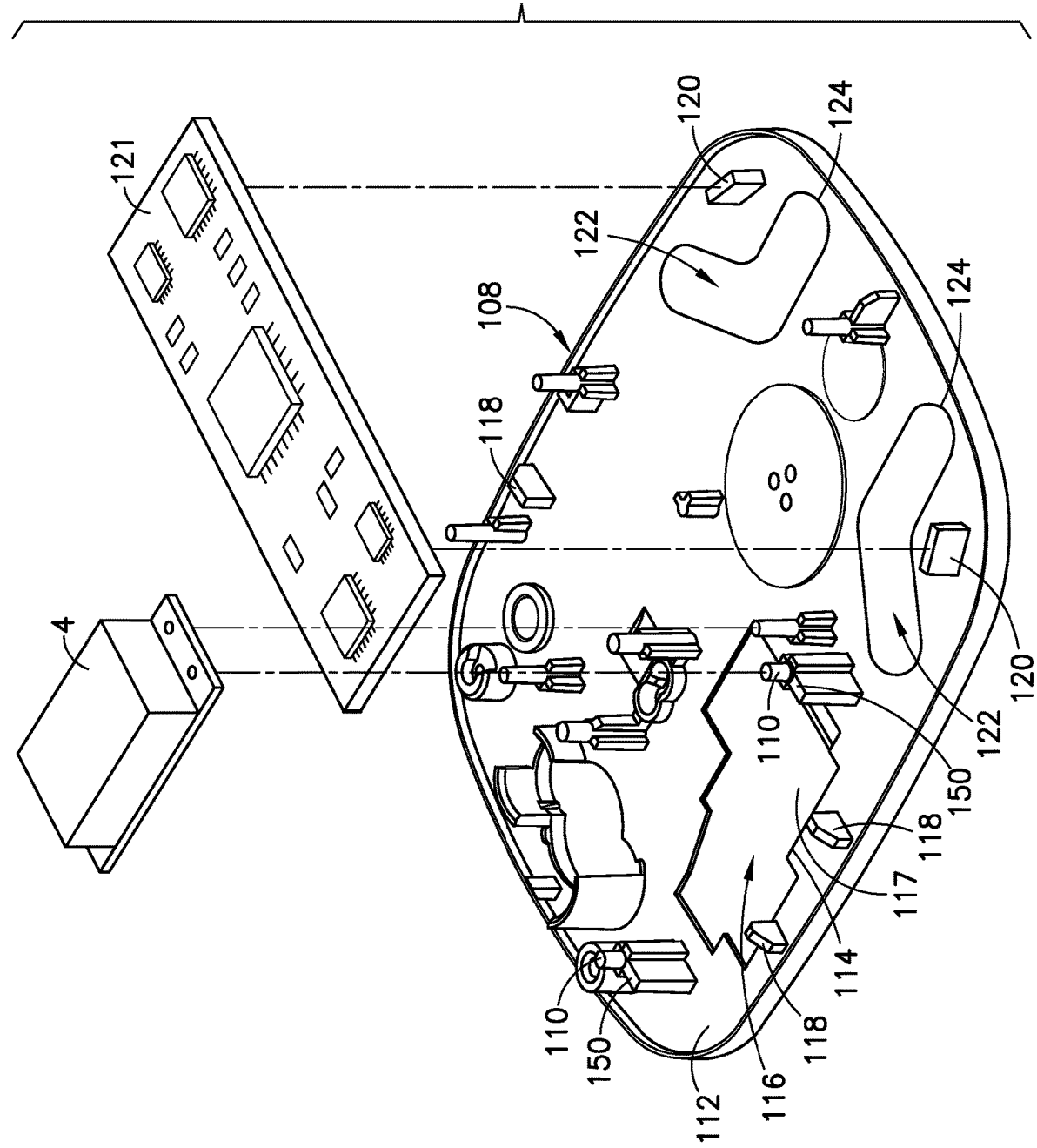
FIG. 7 is a top perspective view of the base of a pump assembly in accordance with one embodiment of the delivery device.
Figure 8:
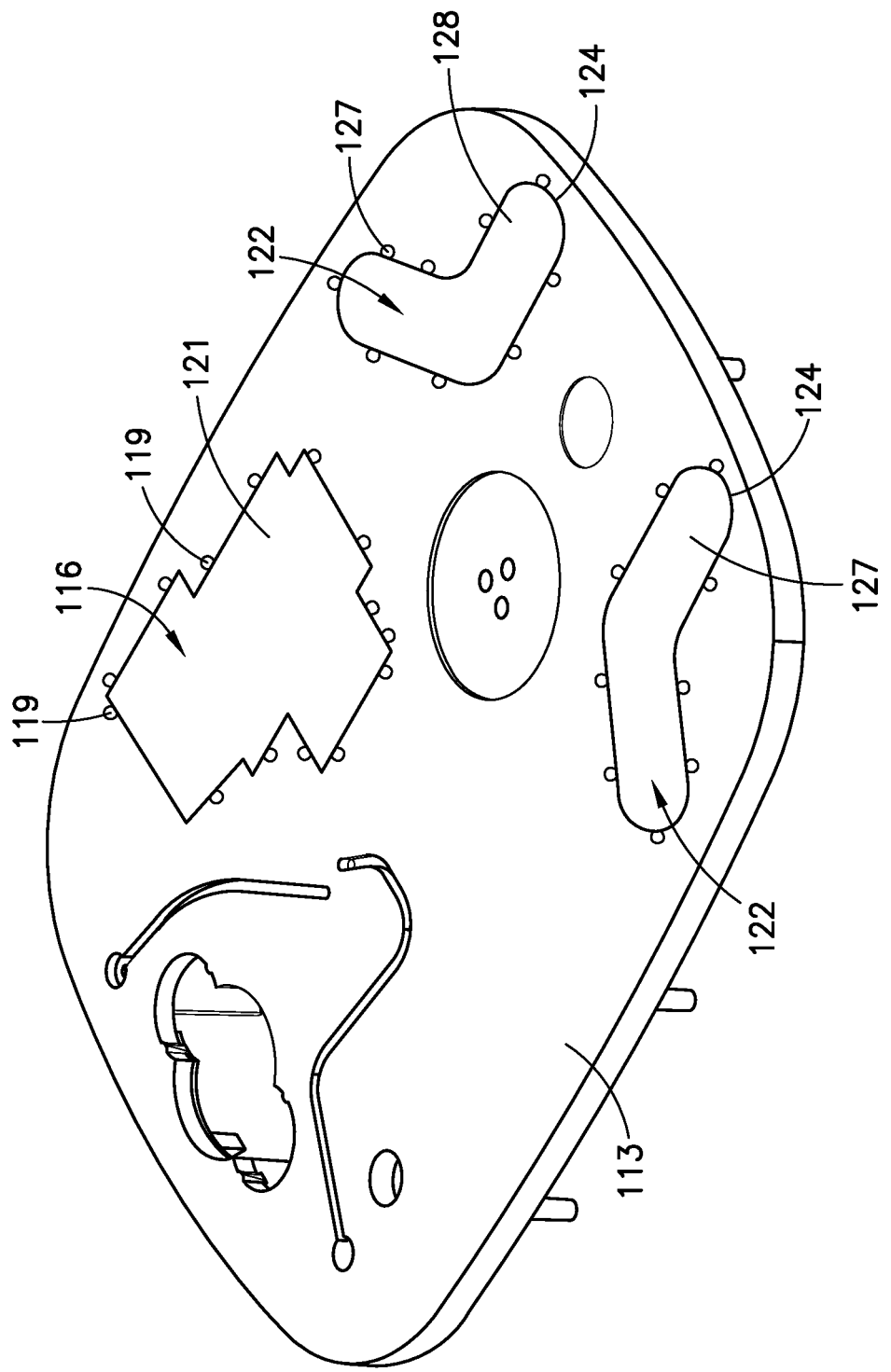
FIG. 8 is a bottom perspective view of the base of the base of FIG. 7.

FIG. 7 is a top perspective view of the base 108 and FIG. 8 is a bottom perspective view of the base in one embodiment. The base 108 is configured to couple to the housing 102 to enclose the various components of the delivery device including the pump mechanism 4 of FIG. 2. As shown in FIG. 7, the base 108 includes mounting posts 110 or other supports for coupling to the components of the pump mechanism 4. The posts 110 project from the top face 112 of the base and are oriented to mount the components of the pump mechanism 4 to the base 108. The posts 110 are positioned for supporting the components of the delivery device including the pump, pump motor, gear box or drive mechanism for the pump, electronic components, switches, timers and batteries. In the embodiment shown in FIG. 7, the posts 110 are spaced apart a distance for supporting the pump mechanism and motor for the pump mechanism.

In the embodiment shown in FIG. 7, a recess 114 is formed in the top face 112 between the posts 110. The recess 114 has a shape and configuration complementing the shape and configuration of the pump mechanism, gearbox or drive mechanism, and the motor for operating the pump mechanism. A noise reducing component of the device is provided by a noise dampening member 116 in the recess 114 to be positioned between the base 108 and the mechanical components such as the pump mechanism, gearbox, or motor for operating the pump mechanism. The noise dampening member 116 is generally positioned proximate the moving components and noise producing components to absorb and dampen noise and vibration and reduce noise and vibration from the delivery device that can otherwise be perceived by the user. In the embodiment shown, the noise dampening member 116 is an elastomeric material that is sufficiently resilient to function as a noise dampening and vibration dampening material to dampen the noise and vibration from the components of the delivery device. The noise dampening material is typically applied as a molded component in the recess 114 with a thickness sufficient to dampen the noise and vibration produced by the pump mechanism, the gearbox of the pump mechanism, and the pump motor.

In the embodiment shown in FIG. 7 and FIG. 8, the recess 114 is defined by an open area in the base 108 where the open area extends between the top face 112 and the bottom face 113. The noise dampening member 116 is molded in the recess 114 and attached or bonded to the base. As shown in the embodiment of FIG. 7, the noise dampening member 116 has a top face 117 that is substantially flat and parallel to the top face 112 of the base 108.

As shown in the embodiment of FIG. 8, the molded noise dampening member 116 has a bottom face 121 that is substantially aligned with the bottom face 113 of the base 108. The bottom face 121 of the noise dampening member 116 can be molded with a plurality of tabs 119 integrally formed with the noise dampening member 116 and embedded within or attached to the bottom face 113 of the base 108 to stabilize and mechanically attach the noise dampening member 116 to the base 108. The bottom face 113 of the base 108 in this embodiment has a plurality of recesses to accommodate the tabs 119 of the noise dampening member 116. The tabs 119 of the noise dampening member 116 are preferably flush with the bottom face of the base and the bottom face of the noise dampening member 116. The bottom face of the noise dampening member is generally flush with the bottom face of the base to form a continuous surface for contacting the patient during use.

Figure 11:
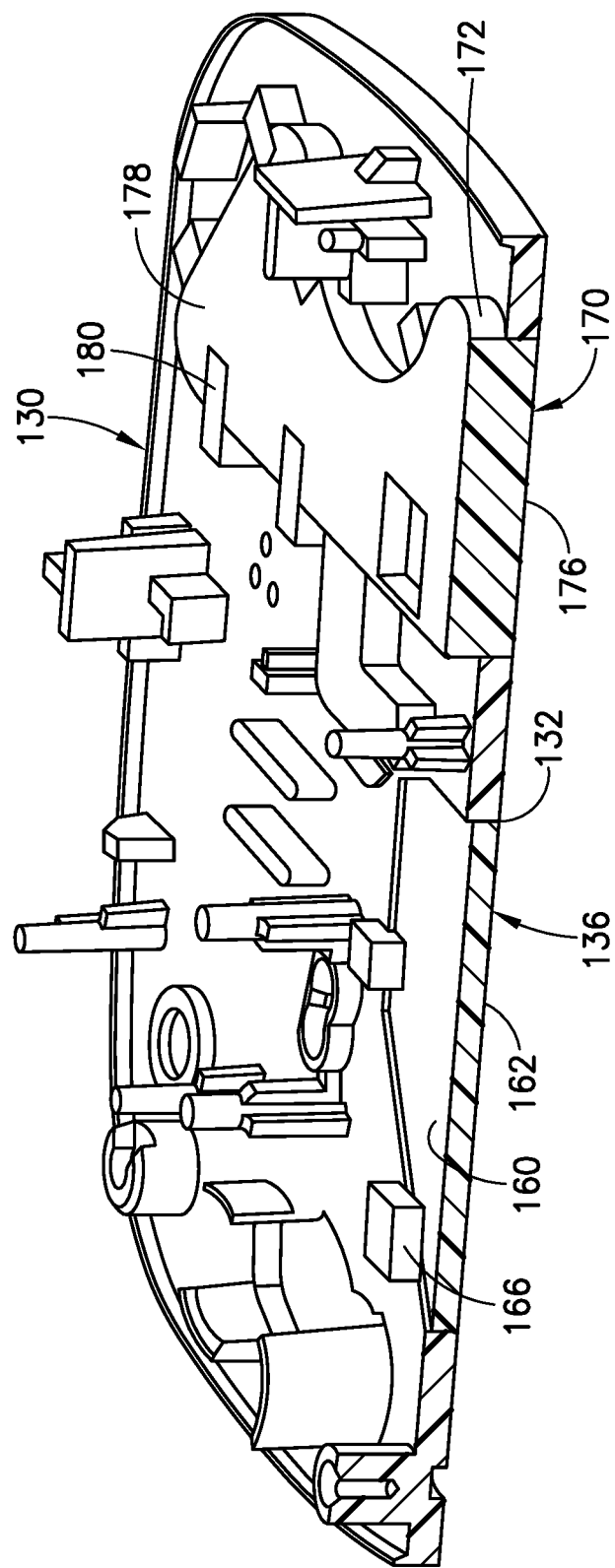
FIG. 11 is top perspective view of the base in cross section showing the noise dampening member.

In the embodiment shown, the base 108 is formed with the recess 114. The noise dampening polymeric material is molded in the recess to form the noise dampening member 116 bonded to the base. The noise dampening member 116 can have a thickness corresponding to the depth of the recess 114 and/or the thickness of the base 108. The noise dampening member 116 can also have a thickness so that the top face 117 of the noise dampening member 116 is recessed with respect to the top face 112 of the base 108 to define a recessed area or cavity for accommodating one or more of the components of the pump mechanism as shown in FIG. 11. In one embodiment, the recessed area has depth so that the pump mechanism does not directly contact the noise dampening member 116. In other embodiments, the noise dampening member can have a thickness to extend upward from the top face 112 of the base 108 such that the top face of the noise dampening member is aligned with or extends from the top face 112 of the base. In another embodiment, the top face 112 of the base 108 can be substantially flat where the noise dampening material can be formed as a layer on the top surface and extend upwardly from the top face of the base 108. In the various embodiments, the noise and vibration producing components of the pump mechanism are position above or proximate the noise dampening member.

The noise dampening member 116 can be a suitable material that is able to absorb and dampen the sound and vibration of the various components of the device and particularly the moving mechanical components of the motor, pump mechanism, and gearbox for operating the pump mechanism. In one embodiment, the noise dampening material is an elastomeric material that is able to reduce the transfer of the vibration, noises, and sounds produced by the components of the pump mechanism through the base and housing. The noise dampening material can be a thermoplastic elastomeric polymer that can be molded directly in or on the base 108 and/or in the recess 114. An example of the thermoplastic elastomer can be a polyurethane elastomer that can be molded, bonded, or coated on the rigid plastic that is used to form the base 108. Other examples of elastomers as the noise dampening material include natural rubber, polybutadiene, neoprene, silicones, polyisobutylene, and styrene-butadiene. The noise dampening material can be flexible to conform to the shape of the surface that supports the noise dampening member.

In one embodiment, the base 108 is an injection molded part made from a rigid plastic material that is able to support and protect the components of the device 100. The noise dampening material can then be molded in the recess 114, onto the base 108, or on other parts by a two-shot molding process as known in the art to apply the noise dampening material to one or more areas on the base 108 or other parts of the device. The noise dampening member 116 is bonded to the supporting surface of the base 108 by the molding process. Alternatively, the noise dampening material is preformed and adhered by a suitable bonding method. In one embodiment, the noise dampening material is applied to selected locations in areas supporting the components that are likely to produce vibrations and sounds that can transfer through the base 108 and/or housing 102. The location of the noise dampening material is selected to absorb vibrations and sounds from mechanical components of the device and reduce the vibrations and sounds perceived by the user. The noise dampening material in one embodiment is selected to be able to adhere sufficiently to the base 108 or other part during use of the device.

In the embodiment shown in FIG. 7, guides 118 are provided that project upwardly from the top face 112 of the base 108 in the vicinity of the noise dampening material 116 and between the posts 110. The guides 118 form members for guiding and mating with the outer cover or housing of the device during assembly. Referring to FIG. 7, shelves 150 are formed with the posts 110 for supporting the pump mechanism, motor, and the gearbox mechanism for the pump mechanism. In the embodiment shown, the shelves 150 have a height to support the motor and gearbox and space the motor and gearbox from the top face of the base 108 and from the top face 117 of the noise dampening material 116. The pump motor and gearbox are generally supported by the posts 110 and the shelves 150 above the noise dampening member without the pump motor and gearbox in direct contact with the top face 112 of the base 108 or the top face 117 of the noise dampening member 116 to reduce vibrations and noise from transferring through the base and housing 102. The noise dampening member 116 is oriented on or in the base 108 to dampen vibrations or sounds of the, pump, motor and/or gearbox or other mechanical components that can be undesirable to the patient. In other embodiments, the motor and gearbox can contact the noise dampening member 116 where the noise dampening material is able to absorb vibrations and noise from the components.

In the embodiment of FIGS. 7 and 8, supports 120 are provided at an end portion of the base 108 for supporting printed circuit boards 121 or other electronic components for operating the motor and pump mechanism. A noise dampening member 122 formed from the noise dampening material is provided between supports 120 to absorb and dampen vibrations and noise produced in the device 100. In the embodiment shown, two noise dampening members 122 are formed at opposite corners of the base 108. In other embodiments the number and location of the noise dampening members 122 can vary depending on the construction of the device and location of the components.

In the embodiment shown, the noise dampening members 122 are formed in corresponding recesses 124 formed in the top face 112 of the base 108. The noise dampening material can be molded within the recesses 124 with the top face 126 of the noise dampening member 122 formed substantially flush with the top face 112 of the base 108. In other embodiments, the noise dampening material can be applied directly on the top face 112 to extend upward from the top face 112 a distance to provide a thickness sufficient to dampen vibrations and noise from the various components of the device. In other embodiments, the top face of the noise dampening member 122 can be recessed relative to the top face of the base.

In the embodiment shown, the recesses 124 define openings extending through the base between the top face 112 and the bottom face 113 of the base 108. The noise dampening members 122 are molded in the recesses 124 with the top face 126 of the noise dampening members 122 aligned with and substantially flush with the top face 112 of the base 108. The bottom face 128 of the noise dampening members 128 are aligned with and substantially flush with the bottom face 113 of the base 108.

The recess 124 as shown in the bottom view of FIG. 8 is formed by side walls extending between the top face 112 and bottom face 113 of the base 108. A plurality of tabs 119 forming lugs are molded integrally with the noise dampening member 116 and extend outwardly to cooperate with the bottom face 113 of the base 108 to assist in mechanically attaching the noise dampening member 116 to the base 108. Tabs 127 are molded on the bottom face 122 of the noise dampening member 122 and extend outward and contact the bottom face 113 of the base 108 for mechanically attaching the noise dampening member 122 to the base 108.

Figure 9:
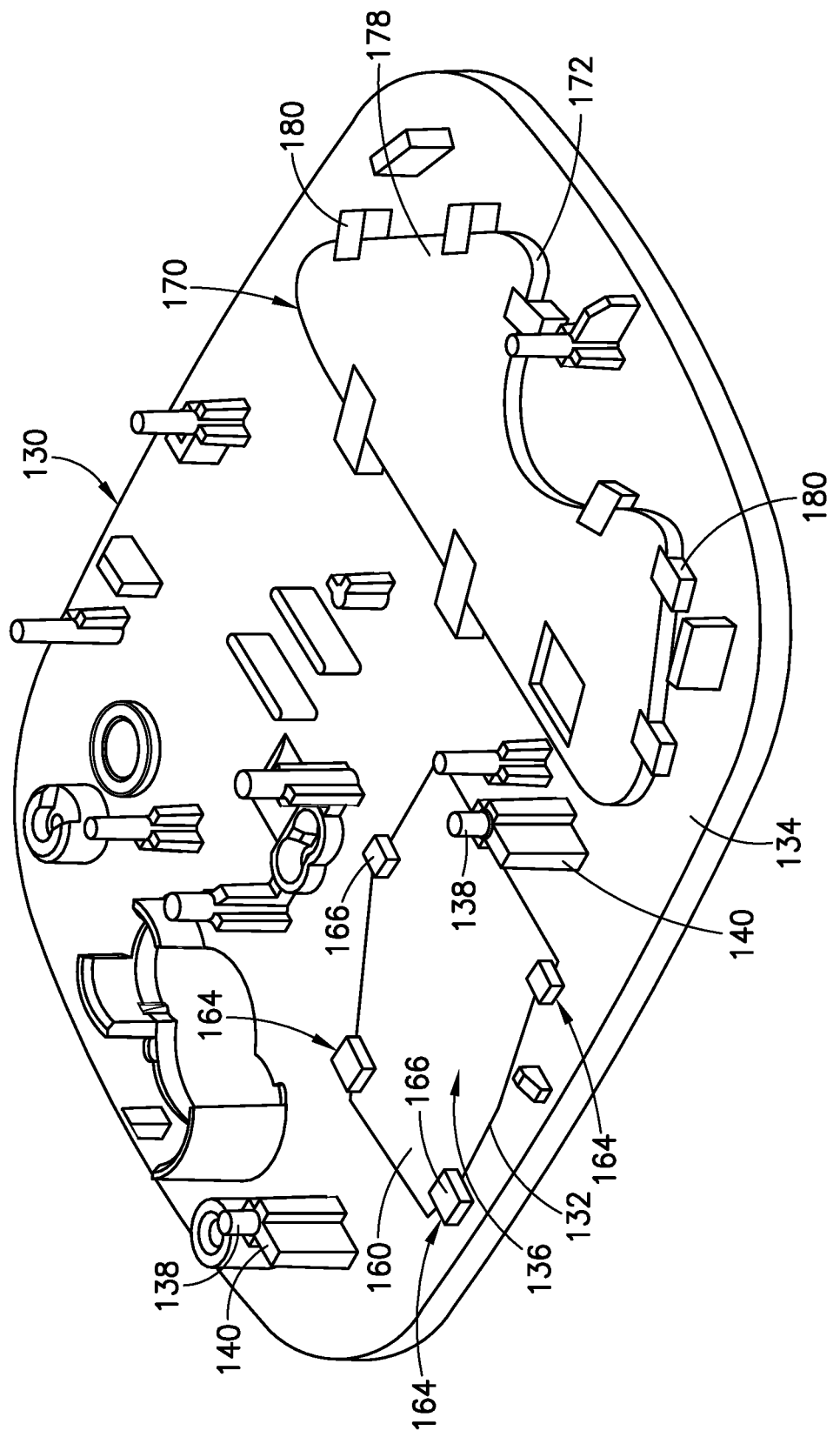
FIG. 9 is a top perspective view of base of a pump assembly in another embodiment of the invention.
Figure 10:
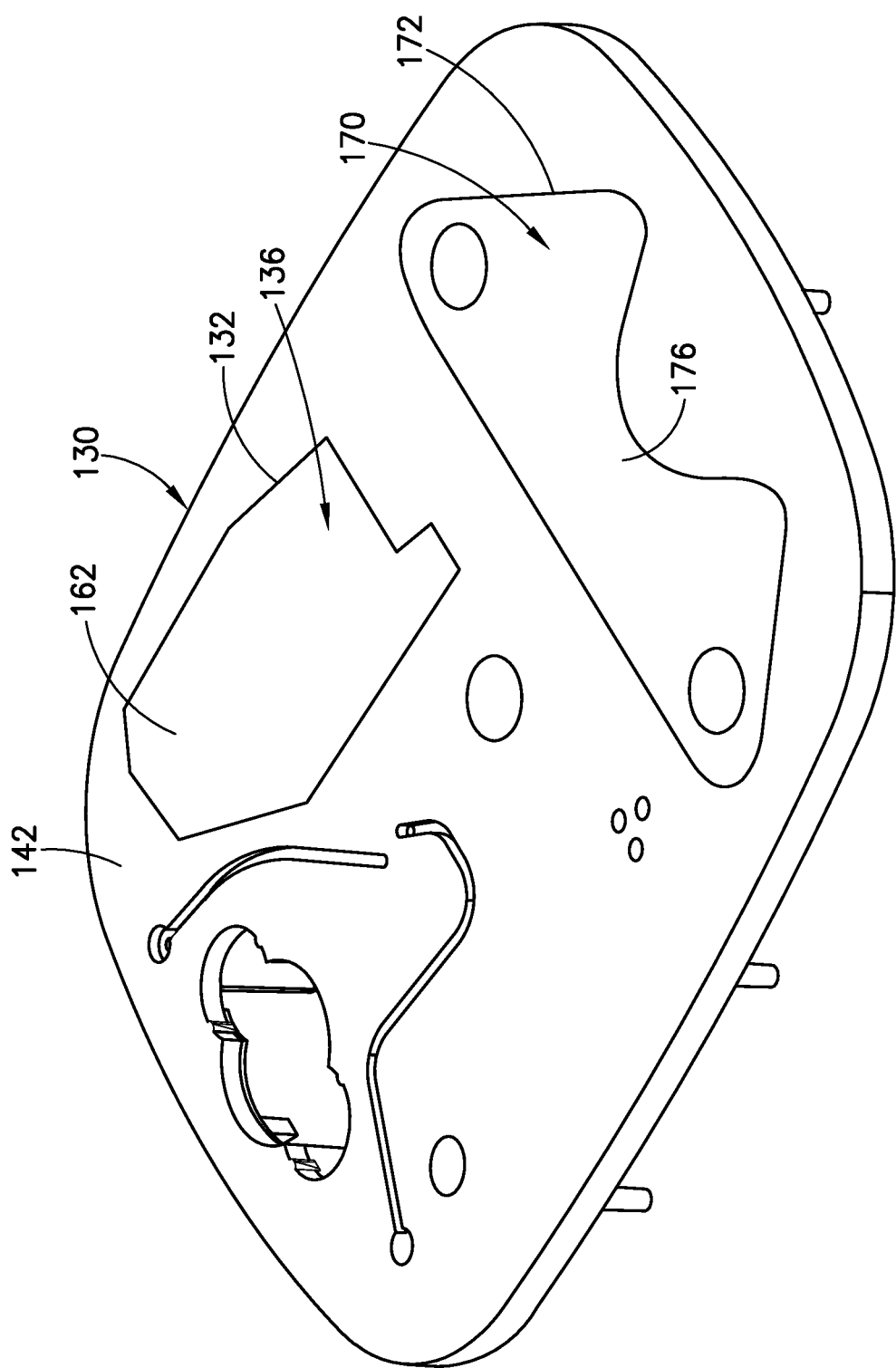
FIG. 10 is a bottom perspective view of the base of the pump assembly of FIG. 9.

Another embodiment of the invention is shown in FIGS. 9-11 where a base 130 is configured for coupling to the housing 102 of the device and supporting the components of the device. As shown in FIG. 9, a recess 132 is formed in the top face 134 of the base 130 receiving a noise dampening member 136 formed from a noise and vibration absorbing material. As in the previous embodiment the noise dampening material is typically a thermoplastic elastomer such a polyurethane elastomer. The recess 132 in the embodiment shown is defined by an opening that extends through the base 130 between the top face 134 and the bottom face 142 of the base 130 as shown in the cross section of FIG. 11.

In the embodiment of FIG. 9 and FIG. 11, the noise dampening member 136 has a thickness relative to the depth of the recess 132 and thickness of the base 130 so that the top face 160 of the noise dampening member 136 is recessed with respect to the top face 134 of the base 130 to form a recessed area to accommodate the pump mechanism. Alternatively, the top face 160 can be flush with the top face 134 of the base 130. The bottom face 162 of the noise dampening member 136 is also shown as being aligned with and substantially flush with the bottom face 142 of the base 130 as shown in FIG. 10 and FIG. 11. Posts 138 form supports that project upward from the top face 134 for supporting mechanical components such as the pump mechanism and gearbox of the pump mechanism. Shelves 140 are oriented around the perimeter of the recess 132 and the noise dampening member 136 for supporting one or more components of the device and to form a gap or space between the noise dampening member 136 and the mechanical components of the device. In the embodiment shown, the shelves 140 are formed with the posts 138 and oriented above the top face of the noise dampening member 136 to space the components of the device from the top face 134 of the base 130 and space the components from the top face 160 of the noise dampening member 136. The top face of the noise dampening member 136 can be recessed relative to the top face of the based to form the recess area or cavity to accommodate a portion of one or more components of the pump mechanism.

As shown in FIG. 9, the noise dampening member 136 is formed with a plurality of projecting tabs 164 that extend upward from the top face 160 of the noise dampening member 136. In the embodiment shown, four such tabs 164 are provided that are formed with a substantially flat top face 166. As shown in FIG. 9, the tabs 164 are spaced around the perimeter of the noise dampening member 136 and extend outward from the perimeter to overlie and contact the top face 134 of the base 130. The tabs 164 are integrally formed with the noise dampening member 136 to assist in mechanically attaching to the base 108.

In the embodiment of FIGS. 9 and 10, the base 130 includes a second noise dampening member 170 at an end portion of the base 130 in the area where the printed circuit boards or other electronic components are supported within the device. As shown in FIGS. 9 and 11, the base 130 is provided with a recess 172 formed by an opening extending through the base 130 and extending between the top face 134 and bottom face 142 of the base 130. The noise dampening member 170 is molded from an elastomeric material within the recess. In the embodiment shown in FIG. 10, the bottom face 176 of the noise dampening member 170 is aligned with and substantially flush with the bottom face 142 of the base 130.

Referring to FIGS. 9 and 11, the noise dampening member 170 has a thickness greater than the thickness of the base 130 where the top face 178 of the noise dampening member 170 extends above the top face 142 of the base 130. The top face 178 of the noise dampening member 170 is formed with a plurality of tabs 180 that extend outwardly from the side of the noise dampening member 170 to overlie the top face 142 of the base 130 as shown in FIGS. 9 and 11 for mechanically attaching to the base.

Figure 13:
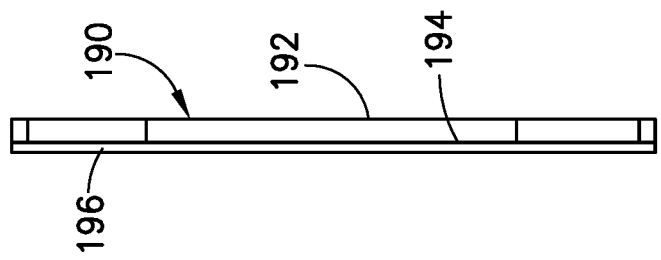
FIG. 13 is an end view of the noise dampening member of FIG. 12.
Figure 12:
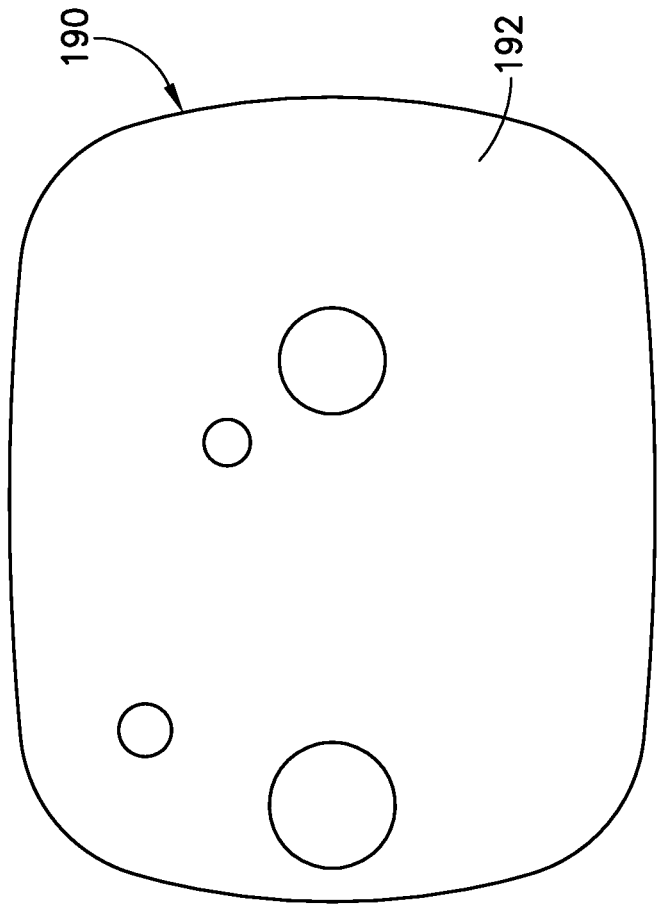
FIG. 12 is a top view of a noise dampening member in another embodiment formed as a separate member that can be attached to the device.

FIGS. 12 and 13 illustrate a further embodiment where the noise dampening member 190 is formed as a separate member and attached or bonded to the device in a suitable location to provide the desired noise dampening and vibration dampening properties. In the embodiment shown in FIG. 12, the noise dampening member 190 is formed as a sheet-like member having an outer or top side 192 and an inner or bottom side 194 having an adhesive or mastic 196 applied to the bottom side for attaching to the selected surface of device. In the embodiment shown, the noised dampening member 190 has shape complementing the shape and dimension of the base and has a thickness sufficient to provide the desired level of noise dampening without interfering with the mounting of the components of the device. The adhesive 196 can be applied to the entire surface of the noise dampening member or only to selected portions depending on the requirements for the device. The noise dampening member can have a shape and dimension to fit in a suitable location in or on the device to dampen sounds. The noised dampening member can be attached to an inner surface of the base within the cavity of the device on an outer face of the base.

FIGS. 14 and 15 illustrate another embodiment of the invention where the noise dampening member 200 has a shape and configuration to cover a portion of the base of the device. The noise dampening member 200 has an outer edge 202 configured to complement the outer dimension of the base with a plurality of cut-outs 204 and openings 206 to accommodate the various tabs, supports and components of the device that project from or are supported by the base as in the previous embodiments. As shown in FIG. 15 an adhesive or mastic layer 208 is applied to a bottom side 210 of the noise dampening member 200 for attaching directly to the base.

The noise dampening materials can be formed from a thermoplastic elastomer as in the previous embodiments and have a thickness and dimension to provide sufficient noise dampening from the mechanical components in the device. In other embodiments, the noise dampening member can have a dimension complementing the dimensions of the top face of the base. In other embodiments, the noise dampening member can be attached to a top surface of the base have a dimension less than the dimension of the top face of the base. In further embodiments, the noise dampening member can be attached to or bonded to a surface of the housing or cover in a selected location to provide the desired noise dampening property.

In the embodiments illustrated, the noise dampening member can be molded or formed within the base and located or positioned at a suitable location where the noise dampening member can dampen the sounds produced by the pump mechanism or outer components that can produce sounds and/or vibrations that can be perceived by the user. The noise dampening material member can be molded in a recess or opening formed in the base and attached directly to the base by suitable mechanisms. The noise dampening member can be spaced from the moving mechanical components or can be positioned between the mechanical components and the base to reduce the noise and vibrations from transferring to the base. In the embodiment shown, the noise dampening member has at least one surface facing the components of the pump mechanism.

Generally the thickness and dimension of the noise dampening member provide the desired noise dampening properties. In the embodiment where the noise dampening member is positioned between the pump mechanism or other noise producing component and the base, the thickness of the noise dampening member is limited by the position of the mechanical components. Where the noise dampening member is positioned in other locations, the thickness of the noise dampening member can be increased to increase the noise dampening properties. The dimension of the noise dampening member can be a suitable size to fit within the boundary or perimeter of the base or other part without interfering with the operation of the device. In other embodiments, the noise dampening member can be attached to a bottom face of the base or at other locations on the outer or inner surfaces of the device.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents. Features of the different embodiments can be combined with other embodiments or features as long as they do not contradict each other.

The invention claimed is:

1. A delivery device, comprising:
a housing;
a base coupled to said housing and forming an enclosure, said base configured for supporting a delivery mechanism, a cannula configured for delivering a substance to a patient, said cannula connected to said delivery mechanism, and a reservoir for the substance to be delivered to the patient, and said reservoir connected to said delivery mechanism, said base configured for supporting at least one component of said delivery mechanism; and
at least one noise dampening member on said base to dampen noise produced by said delivery mechanism;
wherein said at least one noise dampening member is positioned in said base or on said base, and where said at least one noise dampening member has a top surface in said enclosure and a bottom surface facing outwardly from a bottom face of said base.

2. The delivery device according to claim 1, wherein said at least one noise dampening member is positioned between said base and said at least one component of said delivery mechanism.

3. The delivery device according to claim 1, wherein said at least one noise dampening member is a thermoplastic elastomeric material attached or adhered to said base.

4. The delivery device according to claim 1, wherein said at least one noise dampening member includes a plurality of outwardly extending tabs, and where said tabs are directly coupled to a surface of said base.

5. The delivery device according to claim 1, wherein said at least one noise dampening member is formed as a separate member attached to said base by bonding or by an adhesive.

6. The delivery device according to claim 1, wherein said base has a top face coupled to said housing and where said base includes a recess in said top face and where said at least one noise dampening member is received in said recess, and said at least one noise dampening member has a top surface spaced from the top face of said base to define a recessed area in said top face to accommodate said delivery mechanism.

7. The delivery device of claim 1, wherein said base has a top face coupled to said housing, a bottom face, and a recess extending between said top face and said bottom face, and where said at least one noise dampening member is received in said recess.

8. The delivery device of claim 7, wherein said at least one noise dampening member includes a plurality of outwardly extending tabs, said outwardly extending tabs coupled to at least one of said top face and said bottom face.

9. A delivery device, comprising:
a housing;
a base coupled to said housing and forming an enclosure, said base configured for supporting a delivery mechanism, a cannula configured for delivering a substance to a patient, said cannula connected to said delivery mechanism, and a reservoir for the substance to be delivered to the patient, and said reservoir connected to said delivery mechanism, said base configured for supporting at least one component of said delivery mechanism; and
at least one noise dampening member on said base to dampen noise produced by said delivery mechanism;
wherein said base has a top face coupled to said housing, a bottom face, and a recess extending between said top face and said bottom face, and where said at least one noise dampening member is received in said recess; and
wherein said at least one noise dampening member has a top surface facing said enclosure and a bottom surface accessible from said bottom face of said base.

10. A delivery device comprising:
a housing;
a base coupled to said housing and defining an enclosure for accommodating a pump mechanism for delivering a substance to a patient, said base having a top face supporting said pump mechanism, and a bottom face; and
at least one noise dampening member formed in or on said base, and where said pump mechanism is coupled to said top face of said base, where said at least one noise dampening member is positioned between said top face of said base and said pump mechanism;
wherein said at least one noise dampening member has a top surface in said enclosure and a bottom surface facing outward from the bottom face of said base.

11. The delivery device according to claim 10, wherein said at least one noise dampening member is a thermoplastic elastomeric material adhered to said top face of said base.

12. The delivery device according to claim 10, wherein said top face of said base has a recess and where said at least one noise dampening member is received in said recess in said base and adhered directly to a surface of said base.

13. The delivery device of claim 12, wherein said at least one noise dampening member has a plurality of tabs extending outwardly from at least one said noise dampening member where said tabs are coupled to one of said top face or bottom face of said base.

14. The delivery device of claim 10, wherein said top face of said base is coupled to said housing, and where said top face has a plurality of said noise dampening members in said base or on said top face of said base.

15. The delivery device of claim 14, wherein each said plurality of noise dampening members has a plurality of outwardly extending tabs, and where said outwardly extending tabs are coupled to one of said top face or bottom face of said base.

16. The delivery device of claim 15, wherein said plurality of noise dampening members has a top face spaced outwardly from said top face of the base toward said enclosure.

17. The delivery device of claim 10, wherein said at least one noise dampening member is formed as a separate member and is attached to the top face of said base by bonding or by an adhesive.

18. A delivery device comprising:

a housing;

a base coupled to said housing and defining an enclosure for accommodating a pump mechanism for delivering a substance to a patient, said base having a top face supporting said pump mechanism, and a bottom face; and at least one noise dampening member formed in or on said base, and where said pump mechanism is coupled to said top face of said base, where said at least one noise dampening member is positioned between said top face of said base and said pump mechanism;

wherein said top face of said base has a recess and where said at least one noise dampening member is received in said recess in said base and adhered directly to a surface of said base; and wherein said recess extends between said top face and bottom face of said base.

19. The delivery device of 16, wherein said at least one noise dampening member has top surface in said enclosure and a bottom surface aligned with said bottom face of said base.

\* \* \* \* \*